United States Patent
Ziv-Ari et al.

(10) Patent No.: US 10,792,097 B2
(45) Date of Patent: Oct. 6, 2020

(54) ABLATION LINE CONTIGUITY INDEX

(71) Applicant: BIOSENSE WEBSTER (ISRAEL) LTD., Yokneam (IL)

(72) Inventors: Morris Ziv-Ari, Atlit (IL); Shiran Eliyahu, Yokneam Illit (IL); Assaf Rubissa, Misgav (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 557 days.

(21) Appl. No.: 15/274,205

(22) Filed: Sep. 23, 2016

(65) Prior Publication Data

US 2017/0156792 A1 Jun. 8, 2017

Related U.S. Application Data

(60) Provisional application No. 62/262,440, filed on Dec. 3, 2015.

(51) Int. Cl.
*A61B 18/12* (2006.01)
*A61B 18/14* (2006.01)
(Continued)

(52) U.S. Cl.
CPC .......... *A61B 18/1492* (2013.01); *A61B 34/20* (2016.02); *G05B 15/02* (2013.01);
(Continued)

(58) Field of Classification Search
CPC ........ A61B 5/4836; A61B 2018/00636; A61B 2018/00642; A61B 2018/00648;
(Continued)

(56) References Cited

U.S. PATENT DOCUMENTS

| 6,743,225 B2 | 6/2004 | Sanchez et al. |
| 7,306,593 B2 * | 12/2007 | Keidar ..................... A61B 5/06 606/34 |

(Continued)

FOREIGN PATENT DOCUMENTS

| WO | WO 2010/140069 A1 | 12/2010 |
| WO | WO 2012/092275 A1 | 7/2012 |

OTHER PUBLICATIONS

European Search Report dated Apr. 6, 2017 from corresponding European Patent Application No. 16201880.8.
(Continued)

*Primary Examiner* — Daniel W Fowler
(74) *Attorney, Agent, or Firm* — Dergosits & Noah LLP; Todd A. Noah

(57) ABSTRACT

A method for treatment evaluation includes applying energy through a probe to ablate tissue at a plurality of sites in an organ in a body of a patient, thereby creating lesions in the tissue including at least first and second lesions at respective first and second, mutually-adjacent sites. Location coordinates and respective treatment parameters are recorded at each of the sites with respect to the applied energy. Based on the recorded treatment parameters, respective measures of size of the lesions are computed, including at least respective first and second measures of the first and second lesions. An indication of contiguity between at least the first and second lesions is generated responsively to the first and second measures and to a distance between the location coordinates of the first and second sites.

23 Claims, 2 Drawing Sheets

(51) Int. Cl.
*G16H 40/63* (2018.01)
*A61B 34/20* (2016.01)
*G05B 15/02* (2006.01)
*A61B 18/00* (2006.01)

(52) U.S. Cl.
CPC .... *G16H 40/63* (2018.01); *A61B 2018/00351* (2013.01); *A61B 2018/00357* (2013.01); *A61B 2018/00577* (2013.01); *A61B 2018/00648* (2013.01); *A61B 2018/00702* (2013.01); *A61B 2018/00738* (2013.01); *A61B 2018/00779* (2013.01); *A61B 2018/00886* (2013.01); *A61B 2018/00988* (2013.01); *A61B 2018/1467* (2013.01)

(58) Field of Classification Search
CPC .......... A61B 2018/00779; A61B 2018/00886; A61B 2018/00696; A61B 2018/00761; A61B 34/10; A61B 34/20; A61B 34/25; A61B 2034/101
See application file for complete search history.

(56) References Cited

U.S. PATENT DOCUMENTS

| | | | |
|---|---|---|---|
| 8,454,589 B2 | 6/2013 | Deno et al. | |
| 8,900,225 B2 | 12/2014 | Bar-Tal et al. | |
| 2003/0144658 A1* | 7/2003 | Schwartz | A61B 18/1492 606/41 |
| 2004/0147920 A1 | 7/2004 | Keidar | |
| 2005/0256522 A1 | 11/2005 | Francischelli et al. | |
| 2008/0287942 A1* | 11/2008 | Amundson | A61B 18/1492 606/41 |
| 2010/0298826 A1* | 11/2010 | Leo | A61B 5/103 606/41 |
| 2011/0130648 A1 | 6/2011 | Beeckler et al. | |
| 2011/0144524 A1 | 6/2011 | Fish et al. | |
| 2011/0152856 A1* | 6/2011 | Govari | A61B 18/1492 606/34 |
| 2012/0029504 A1* | 2/2012 | Afonso | A61B 18/1492 606/34 |
| 2012/0209260 A1* | 8/2012 | Lambert | A61B 18/1492 606/41 |
| 2014/0081262 A1* | 3/2014 | Koblish | A61B 18/1492 606/41 |
| 2014/0163543 A1* | 6/2014 | Allison | A61B 18/1492 606/33 |

OTHER PUBLICATIONS

European Examination Report dated Apr. 20, 2018 from corresponding European Patent Application No. 16201880.8.

* cited by examiner

ABLATION LINE CONTIGUITY INDEX

CROSS-REFERENCE TO RELATED APPLICATION

This application claims the benefit of U.S. Provisional Patent Application 62/262,440, filed Dec. 3, 2015, which is incorporated herein by reference.

FIELD OF THE INVENTION

The present invention relates generally to systems and methods for invasive medical treatment, and specifically to tracking and evaluating such treatment.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intracardiac ablation therapy are commercially available, such as the CARTO™ system offered by Biosense Webster Inc. (Diamond Bar, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus to keep track of the progress of the procedure.

Various measures have been proposed for guiding and assessing the quality of ablation lesions. For example, U.S. Pat. No. 6,743,225 describes methods in which electrical activity of the cardiac tissue is measured proximate the lesion site during an ablation treatment, and the measurements are then compared to determine whether the lesion is clinically efficacious so as to be able to block myocardial propagation. The methods can include obtaining the measurements and performing the ablation therapy while the subject is experiencing atrial fibrillation and may measure the standard deviation of the electrogram signal.

As another example, U.S. Pat. No. 8,454,589 describes a system and method for assessing effective delivery of ablation therapy to a tissue in a body. A 3D anatomical map of the tissue is generated and displayed. An index is generated corresponding to a location and indicating a state of ablation therapy at the location. The index may be derived from factors such as the duration an ablation electrode is present at the location, the amount of energy provided, the degree of electrical coupling between the electrode and the tissue, and temperature. A visual characteristic (e.g., color intensity) of a portion of the anatomical map corresponding to the location is altered responsively to the index.

As yet another example, U.S. Pat. No. 8,900,225, whose disclosure is incorporated herein by reference, describes a method for performing a medical procedure in which a probe into contact with an organ in a body of a patient. A map of the organ is displayed, and the location of the probe relative to the map is tracked. A therapy is applied via the probe at multiple tissue sites in the organ with which the probe is brought into contact. Stability of the contact between the probe and the tissue sites is assessed while applying the therapy. The map is automatically marked, responsively to the assessed stability, to indicate the tissue sites at which the therapy was applied.

SUMMARY

Embodiments of the present invention that are described hereinbelow provide methods and systems for quantitative evaluation of invasive therapies.

There is therefore provided, in accordance with an embodiment of the invention, a method for treatment evaluation, which includes applying energy through a probe to ablate tissue at a plurality of sites in an organ in a body of a patient, thereby creating lesions in the tissue including at least first and second lesions at respective first and second, mutually-adjacent sites. Location coordinates and respective treatment parameters are recorded at each of the sites with respect to the applied energy. Based on the recorded treatment parameters, respective measures of size of the lesions are computed, including at least respective first and second measures of the first and second lesions. An indication of contiguity is generated between at least the first and second lesions responsively to the first and second measures and to a distance between the location coordinates of the first and second sites.

In the disclosed embodiments, applying the energy includes applying radio-frequency electrical energy through the probe while the probe contacts the tissue at each of the sites. In one embodiment, recording the treatment parameters includes measuring a force exerted by the probe against the tissue, a power of the electrical energy, and a temporal duration of application of the energy. Computing the respective measures may include computing an integral over the temporal duration of a product of the force raised to a first non-unity exponent and the power raised to a second non-unity exponent.

In some embodiments, applying the energy includes creating a line of the lesions in the tissue, and generating the indication includes evaluating an integrity of the line by computing the indication of contiguity between neighboring pairs of the lesions along the line.

Additionally or alternatively, generating the indication includes computing the indication while applying the energy, and controlling application of the energy responsively to the indication. In one embodiment, applying the energy includes, after having created the first lesion, continuing to apply the energy at the second site until the computed indication is within a predefined target range.

In some embodiments, generating the indication includes computing a weighted comparison between the first and second measures of the size of the lesions and the distance between the location coordinates of the first and second sites. In one embodiment, computing the weighted comparison includes weighting each of the first and second measures responsively to a thickness of the tissue at each of the first and second sites. Alternatively, computing the weighted comparison includes weighting each of the first and second measures depending upon anatomical locations of the first and second sites.

In a disclosed embodiment, applying the energy includes ablating myocardial tissue in a heart of the patient.

There is also provided, in accordance with an embodiment of the invention, apparatus for performing a medical treatment, including an invasive probe, which is configured to apply energy to ablate tissue at a plurality of sites in an organ in a body of a patient, thereby creating lesions in the tissue including at least first and second lesions at respective first and second, mutually-adjacent sites. A processor is coupled to the probe and is configured to record location coordinates and respective treatment parameters at each of the sites with respect to the applied energy, and to compute, based on the recorded treatment parameters, respective measures of size of the lesions, including at least respective first and second measures of the first and second lesions, and to generate an indication of contiguity between at least the first and second lesions responsively to the first and second measures and to a distance between the location coordinates of the first and second sites.

There is additionally provided, in accordance with an embodiment of the invention, a computer software product, including a computer-readable medium in which program instructions are stored, which instructions are configured to be read and executed by a processor that is coupled to an invasive probe for ablating tissue at a plurality of sites in an organ in a body of a patient, thereby creating lesions in the tissue including at least first and second lesions at respective first and second, mutually-adjacent sites. The instructions cause the processor to record location coordinates and respective treatment parameters at each of the sites with respect to the applied energy, and to compute, based on the recorded treatment parameters, respective measures of size of the lesions, including at least respective first and second measures of the first and second lesions, and to generate an indication of contiguity between at least the first and second lesions responsively to the first and second measures and to a distance between the location coordinates of the first and second sites.

The present invention will be more fully understood from the following detailed description of the embodiments thereof, taken together with the drawings in which:

DETAILED DESCRIPTION OF EMBODIMENTS

Overview

Figure 1:
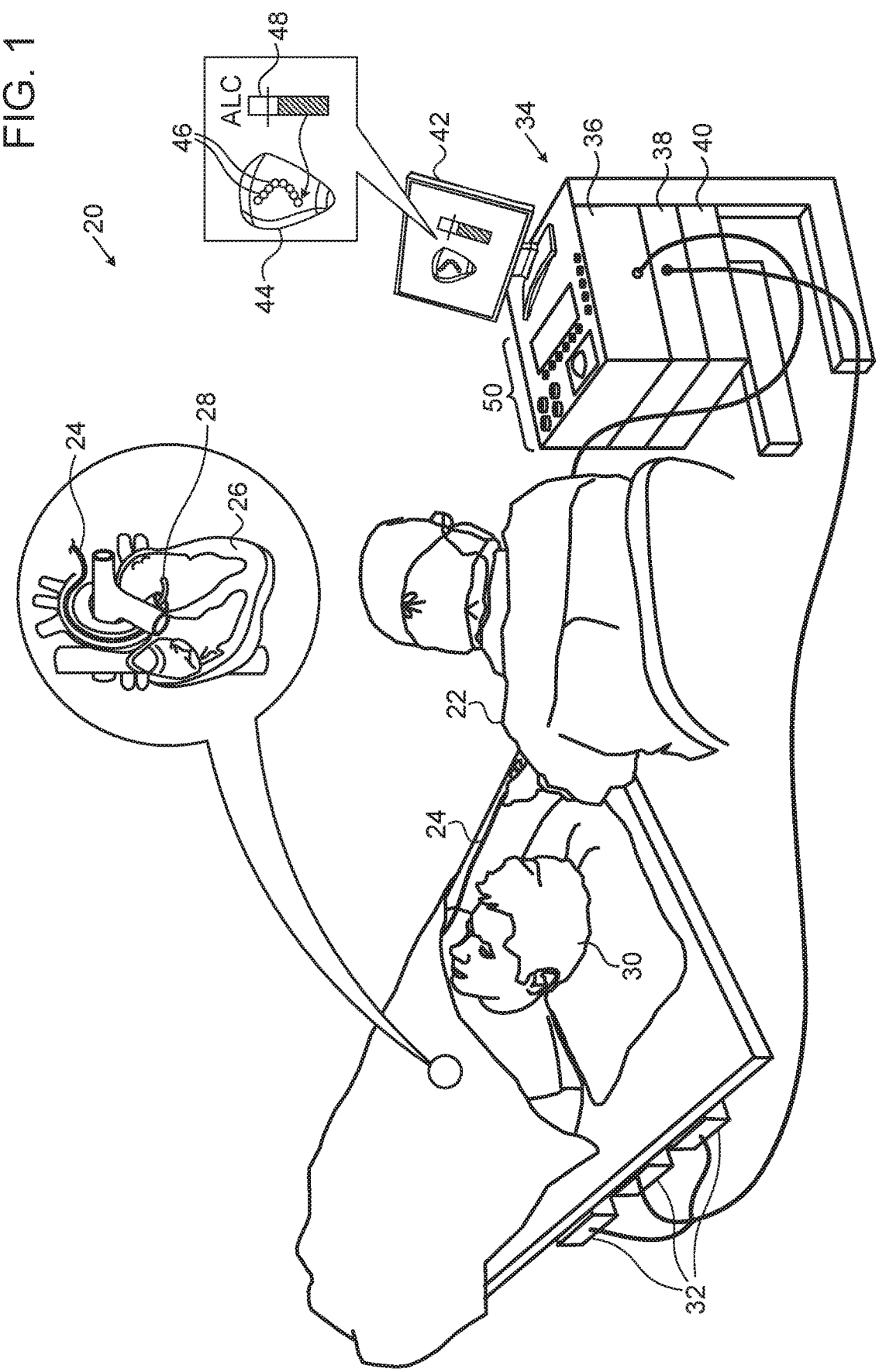
FIG. 1 is a schematic pictorial illustration of a system for intracardiac ablation, in accordance with an embodiment of the invention.

The embodiments of the present invention that are described hereinbelow relate to evaluating lesions that are created in tissue by applying energy through a probe, such as a catheter, to the tissue at multiple sites in an organ in the body of a patient. The disclosed embodiments refer particularly to lesions created in myocardial tissue in the heart by applying radio-frequency (RF) energy through a catheter, which contacts the tissue at each of the lesion sites. The principles of the present invention, however, may also be applied, mutatis mutandis, to other sorts of ablation therapies.

As noted above in the Background section, various measures have been proposed for estimating the size of ablation lesions on the basis of treatment parameters recorded while ablating the tissue. In particular, the inventors have found it useful when evaluating RF ablation to estimate lesion size based on the force exerted by the ablation probe against the tissue, the power of the RF electrical energy, and the temporal duration of application of the energy. In this regard, U.S. patent application Ser. No. 15/177,826, filed Jun. 9, 2016, which is assigned to the assignee of the present patent application and whose disclosure is incorporated herein by reference, describes an "ablation index," which gives a measure of the depth of an ablation lesion as an integral over the temporal duration of the product of the force raised to one non-unity exponent and the power raised to another non-unity exponent. This particular ablation index can be used advantageously in the embodiments described herein, but the principles of the present invention may similarly be applied using other sorts of measures to estimate lesion size.

Such ablation size measures by themselves, however, do not provide a complete picture. In intracardiac ablation procedures, for example, the cardiologist will typically create a line of lesions in the myocardium in an attempt to cut off an arrhythmic current path. In such cases, it is desirable that the lesions be close enough together to create a contiguous block, without gaps through which currents can pass, but not so close as to cause excessive tissue damage. (In this sense, the line of lesions may be only as strong as its weakest link.) At the same time, the lesions should extend through the tissue deeply enough to provide complete blockage, but not so deeply as to create a risk of perforating the heart wall.

In embodiments of the present invention, a measure of lesion size (such as the ablation index) and the location coordinates of each individual lesion in a line is used in assessing the contiguity of the line. "Contiguity" in this sense refers to the extent of overlap between adjacent lesions, which is a function of both the distance between lesion locations and the sizes (depth and width) of the lesions. Insufficient overlap leaves gaps in the tissue between the adjacent lesions through which activation currents can pass, with the result that arrhythmic pathways may reconnect after the ablation procedure. (This sort of phenomenon is common in ablation of lines around the pulmonary veins and is referred to as pulmonary vein reconnection, or PVR.) Excessive overlap can lead to undesired tissue damage and even perforation of the heart wall.

Specifically, in the disclosed embodiments, an ablation line contiguity index (ALCI) is computed to indicate the contiguity between neighboring lesions. For this purpose, a processor computes respective measures of size of the lesions created by a probe at multiple sites, and then generates the ALCI as an indication of contiguity between pairs of mutually-adjacent lesions based on the respective measures of lesion size and the distance between the location coordinates of each pair lesion sites. Typically, the ALCI reflects a weighted comparison (as a quotient or difference, for example) between the measures of size of the lesions and the distance between their location coordinates. The weighting may depend on the thickness of the tissue at the ablation sites and/or on the anatomical location of the sites.

The disclosed embodiments thus assist the operating physician in avoiding both insufficient and excessive overlap by providing a single number, the ALCI, which gives a quantitative indication of the relation between lesion size and inter-lesion distance. The ALCI combines both transmurality and contiguity information of given RF lesions when ablating in the heart chambers.

This ALCI can be applied in various ways to improve the quality of ablation treatments: Retrospectively, the ALCI can be used in evaluating the integrity of a line of lesions that a cardiologist has created in a given procedure and thus to identify weak links in the ablation chain. Prospectively, it can be used as a tool for target-guided ablation when performing pulmonary vein isolation or when creating any isolation line in electrophysiology procedures. For such purposes, the ALCI can be computed on-line, during a procedure, and used in controlling the energy that is applied at each site (either automatically or under user control).

System Description

FIG. 1 is a schematic, pictorial illustration of a cardiac mapping and ablation system 20, which operates in accordance with an embodiment of the invention. System may be based, for example, on the above-mentioned CARTO system, with suitable additions to the system software. System 20 comprises a probe, such as a catheter 24, and a control console 34. In the embodiment described hereinbelow, catheter 24 is used in ablating sites of arrhythmias in one or more chambers of a heart 26 of a patient 30. Alternatively, catheter 24 or other suitable probes may be used, mutatis mutandis, for other therapeutic purposes in the heart or in other body organs.

An operator 22, such as a cardiologist, inserts catheter 24 through the vascular system of patient 30 so that the distal end of the catheter enters a chamber of heart 26. Operator 22 advances the catheter so that an electrode 28 at the distal tip of the catheter engages endocardial tissue at desired ablation sites. Catheter 24 is typically connected by a suitable connector at its proximal end to console 34, and specifically to a radio frequency (RF) generator 36, which generates RF energy for transmission via catheter 24 to electrode 28. Operator 22 actuates RF generator 36 to ablate tissue at suspected sites of arrhythmia in the heart.

In this pictured embodiment, system 20 uses magnetic position sensing to determine position coordinates of the distal end of catheter 24 inside heart 26. For this purpose, a driver circuit 38 in console 34 drives field generators 32 to generate magnetic fields within the body of patient 30. Typically, field generators 32 comprise coils, which are placed below the patient's torso at fixed, known positions. These coils generate magnetic fields in a predefined working volume that contains heart 26. A magnetic field sensor (not shown) within the distal end of catheter 24 generates electrical signals in response to these magnetic fields. A signal processor 40 processes these signals in order to determine the position coordinates of the distal end of catheter 24, typically including both location and orientation coordinates. This method of position sensing is implemented in the above-mentioned CARTO system and is well known in the art. Alternatively or additionally, system 20 may use other methods of position sensing that are known in the art, such as ultrasonic or electrical impedance-based methods.

In addition, catheter 24 may comprise a force sensor (not shown) in its distal end, for measuring the contact force between the catheter tip and the wall of heart 26. The SmartTouch™ catheter developed by Biosense Webster Inc. for the CARTO system offers this sort of capability. A catheter of this sort is described, for example, in U.S. Patent Application Publication 2011/0130648, whose disclosure is incorporated herein by reference. The force measurement is useful in ensuring that electrode 28 is in sufficiently firm contact with the heart wall to effectively transfer RF energy and ablate the heart tissue. The force measurements are also used by processor 40 in computing the ablation index of each ablation lesion created in heart 26.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26. The map may indicate cardiac electrophysiological activity measured by catheter 24, as well as providing visual feedback regarding the position of the catheter in the patient's body and status information and guidance regarding the procedure that is in progress. Other parameters that may be measured by catheter 24 and by other elements of system 20 and shown on display 42 may include, for example, contact force between the catheter and heart tissue, electrical impedance of the heart tissue, local temperature, and RF power delivered through the catheter.

Processor 40 assesses the parameters that it receives from system 20 as indicators of the adequacy of ablation at each treated site in heart 26. When the ablation parameters at a given site meet certain predefined criteria, the processor automatically places a tag 46 on map 44 to indicate the site. The processor may vary the appearance of marks 46 (such as their color) in response to the parameters at each site. The criteria for automatic marking of the ablation sites may be preconfigured, or they may, alternatively or additionally, be set by operator 22, typically using user interface controls 50 and on-screen menus. Additionally or alternatively, operator 22 uses controls 50 to instruct processor to place tags 46 at ablation sites.

In any case, processor 40 records the location coordinates and ablation treatment parameters of each site for purposes of display, as well as computation of the ablation index at each site. For each pair of neighboring lesions, processor 40 computes an ablation lesion contiguity index (ALCI), based on the respective ablation indices and on the distance between the location coordinates of the lesion sites. In FIG. 1, the ALCI is represented by a graphical icon 48, which shows the increase in the ALCI value over time as operator 22 applies RF energy to the second of the pair of sites. For example, as shown in the figure, icon 48 may present a target value of the ALCI, thus prompting operator 22 to continue the treatment until the target value is reached, but not beyond this target value. Additionally or alternatively, processor 40 may automatically control the treatment parameters until the ALCI reaches the target value. Further additionally or alternatively, processor saves the final ALCI value computed for each neighboring pair of lesions for retrospective evaluation.

Although in the illustrated embodiment, catheter 24 is manipulated manually by operator 22, system 20 may alternatively or additionally comprise an automated mechanism (not shown) for maneuvering and operating the catheter within the body of patient 30. In such embodiments, processor 40 generates a control input for controlling the motion of catheter 24 based on the signals provided by the magnetic field sensor in the catheter and other system parameters, such as those mentioned above.

Computation and Application of the ALCI

Various relations have been proposed for estimating the size of such lesions based on ablation parameters, and one of these relations is described in detail hereinbelow. Those having ordinary skill in the art will be aware of other relations. Such relations typically assume that the size S of the lesion will be a function of the force F applied by the catheter to the tissue, the electromagnetic power P dissipated during the ablation procedure, and the time T of the procedure. (Although the relation involves power P, typically the power is measured indirectly by measuring current used for the ablation.) A simple relation of this sort is S=K·F·P·T, wherein K is a constant of proportionality.

The embodiments described hereinbelow make use of the ablation index defined in the above-mentioned U.S. patent application Ser. No. 15/177,826, which indicates the depth of an ablation lesion in the following terms:

$$\text{Depth}^\gamma(T) = C \int_0^T CF^\alpha(t) P^\beta(t) dt \quad (1)$$

Here "Depth" is the depth of the lesion in mm; and γ is a numerical exponent not equal to 1 (unity). The remaining terms are defined as follows, with units given in the table below:

C is a constant of proportionality;

CF(t) is the value of the instantaneous contact force, at a time t, that is applied to the tissue by the catheter during the ablation;

P(t) is a value of the instantaneous power, at a time t, dissipated during the ablation; and α, β are numerical exponents having values not equal to 1 (unity).

TABLE I

| Variable | Units |
| --- | --- |
| CF(t) | g (grams) |
| P(t) | W (watts) |
| t, T | s (seconds) |
| C | $\dfrac{mm^3}{g \cdot W \cdot s}$ |
| α, β, γ | dimensionless |

U.S. patent application Ser. No. 15/177,826 also provides clinical data with regard to the ablation index, giving values for the parameters used in the equation, as well as approximations that can be used in computing and updating the depth. In experimental evaluation described in this application, it was found that the following parameter values give good results in providing an accurate estimate of the actual lesion depth: γ=2.83; α=0.68; β=1.63;

$$C = \frac{1}{531.88}.$$

Furthermore, it was found that the relation between lesion depth and width (i.e., the diameter in the tissue plane) could be estimated by a conversion factor ConvF, which typically (though not necessarily) has a value of about 1.5, depending on tissue characteristics, such as thickness, and anatomical location. In other words, the lesion diameter is approximately equal to ConvF*Depth(T) 1.5*Depth(T), wherein the ablation index Depth(T) is given by formula (1) using the above parameters.

In the description that follows, the ablation index (AI) is taken, for the sake of convenience, to be 100*Depth(T), as defined above. Alternatively, however, other ablation indices may be developed to estimate the lesion diameter based on the force, power, and time parameters outlined above, as will be apparent to those skilled in the art; and the use of such alternative indices in evaluating ablation line contiguity is considered to be within the scope of the present invention.

Figure 2:
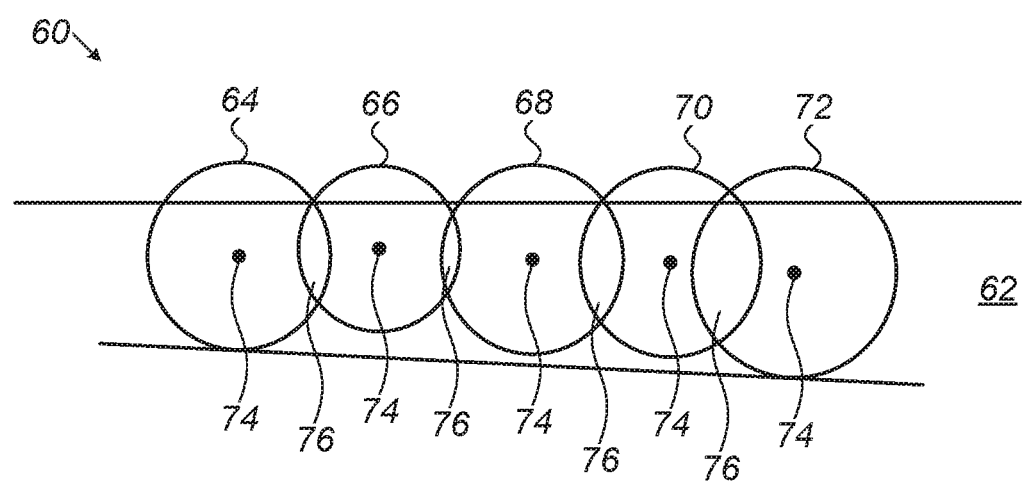
FIG. 2 is a schematic, sectional illustration of a sequence of ablation lesions in myocardial tissue, illustrating a method for computation of an ablation line continuity index, in accordance with an embodiment of the invention.

FIG. 2 is a schematic, sectional illustration of a sequence 60 of ablation lesions 64, 66, 68, 70, 72 in myocardial tissue 62, illustrating a method for computation of an ablation line continuity index, in accordance with an embodiment of the invention. The lesions are arranged in a line, with respective center points 74 corresponding to the sites to which electrode on catheter 24 is applied in order to create the lesions. It is assumed that the purpose of this line of lesions is to break an arrhythmic conduction pathway in tissue 62.

Both the lesion sizes and the spacing between the center points of adjacent lesions can vary, depending on where operator 22 positions catheter 24 in the course of the ablation procedure and on the ablation parameters (such as contact force, power and duration) applied at each site. The extent of an overlap 76 between adjacent lesions varies as a function of the relation between the actual center-to-center distance and the lesion sizes.

The ablation line contiguity index (ALCI), as defined herein, provides a measure of this overlap. In relation to FIG. 2, this ALCI will satisfy the following relation:

$$ALCI_{70\text{-}72} > ALCI_{68\text{-}70} > ALCI_{64\text{-}66} > ALCI_{66\text{-}68}$$

(Here the subscripts indicate the pair of lesions over which each ALCI value is computed.) The risk of reconnection of the arrhythmic pathway between a given pair of lesions increases with decreasing ALCI. As noted earlier, processor 40 in system 20 records the ablation site locations (center points 74 marked in FIG. 2) and ablation parameters applied at each site and automatically computes the ALCI values, either in real time during a procedure or retrospectively, and thus provides an assessment of ablation line quality. The risk of reconnection over the entire ablation line typically depends on the weakest link of the chain, i.e., $ALCI_{66\text{-}68}$ in the above example.

A desired degree of overlap can be determined empirically, and this overlap target can be applied in defining a target value of the ALCI. When the actual ALCI value is above this target value, the likelihood of reconnection is very small. ALCI values much higher than the target value (for example, by 50% or more, or equivalently, ALCI values corresponding to 50% more overlap than the target fraction of overlap) are to be avoided due to the risks of excessive tissue damage and possible perforation.

The inventors have found that the following formula gives good results in assessing contiguity and predicting the likelihood of reconnection between two lesions i and j:

$$\% \, ALC \, \text{Index} = \frac{OC * ConvF * \dfrac{AI_i + AI_j}{2}}{100 * \text{Distance}} * 100$$

In this formula, the term "Distance" is the center-to-center distance between adjacent ablation sites, as indicated by the corresponding tags 46, for example. $AI_i$ and $AI_j$ are the respective ablation indices of the lesions, and the factor of 100 (which in any event cancels out) is introduced for compatibility with the depth-based formula for AI, as defined above. The term OC is an overlap coefficient, which is chosen depending on the desired overlap between adjacent lesions and is typically in the range of 0.5 or higher.

Specifically, assuming the desired degree of overlap between adjacent lesions is 50%, and OC is set to the value 0.5, the ALCI computed using the above formula will have the value one when the lesion sizes in relation to the distance between the lesions give a 50% overlap. In other words, in this example, when ALCI=1 (100%), the average radius of the two adjacent lesions will be equal to the distance between the lesion center points. A smaller value of ALCI will mean that the average radius is less than the distance, while ALCI>1 means that the average radius is greater than the distance.

Alternatively, if OC is set to a value greater than 0.5 (e.g., OC=0.7), ALCI will reach the value one when there is a smaller degree of overlap between adjacent lesions (30% in the case of OC=0.7). Typically, the physician or another operator of the ablation system can set OC to whatever value is desired in order to give satisfactory results. For example, the optimal value of OC may vary for different regions of the heart depending on the heart wall thickness.

Other formulation of the ALCI can also be used for similar purposes and are considered to be within the scope of the present invention. For example, the following formula is useful in taking into account the differences between the anatomical locations of a pair of neighboring lesions:

$$\% \text{ ALC Index} = \frac{OC * \frac{ConvF_i * AI_i + ConvF_j AI_j}{2}}{100 * \text{Distance}} * 100$$

In this case, a different conversion factor, $ConvF_i$ or $ConvF_j$, is applied to each site.

As another example, the following difference formulation can be used:

$$ALC \text{ index} = OC * ConvF * \frac{AI_i + AI_j}{2} - 100 * \text{Distance}$$

In this case, however, the target value of the ALCI will be zero, rather than one as in the previous example, with values greater than zero giving a high likelihood that reconnection will not occur.

As explained earlier, the ALCI can be used clinically in a variety of ways, for example:

Following an ablation procedure, the ALCI can be computed using the stored ablation locations and parameters at each location, and can then be applied in evaluating the results and assessing the likelihood of reconnection, as well as identifying the location or locations that are most at risk for reconnection.

During an ablation procedure, the ALCI can be computed prospectively and used in guiding the physician to choose the next ablation location optimally, given a certain set of ablation parameters (such as force, ablation power, and duration) that are to be applied or, alternatively, the desired AI value for the next lesion. In other words, assuming all lesions are to be created with a certain target AI value, as defined above, the prospectively-computed ALCI indicates the optimal distance to the next location.

Additionally or alternatively, the ALCI can be computed in real time, while ablation is in progress at a given size, given the current catheter location and the known location and AI of an adjacent lesion. As the ablation proceeds over time, with a given contact force and power level, the AI of the current lesion gradually increases, and so does the ALCI. Ablation continues until the ALCI reaches the predetermined target value.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for treatment evaluation, comprising:
applying energy through a probe to ablate tissue at a plurality of sites in an organ in a body of a patient, thereby creating lesions in the tissue including at least first and second lesions at respective first and second, mutually-adjacent sites;
recording location coordinates and respective treatment parameters at each of the sites with respect to the applied energy;
based on the recorded treatment parameters, computing respective measures of size of the lesions, including at least respective first and second measures of the first and second lesions; and
generating an indication of contiguity between at least the first and second lesions responsively to the first and second measures and to a distance between the location coordinates of the first and second sites, the generated indication of contiguity comprising at least one computed value, the at least one computed value based at least on the respective size measurements of the lesions and the distance between the location coordinates of the first and second sites.

2. The method according to claim 1, wherein applying the energy comprises applying radio-frequency electrical energy through the probe while the probe contacts the tissue at each of the sites.

3. The method according to claim 2, wherein recording the treatment parameters comprises measuring a force exerted by the probe against the tissue, a power of the electrical energy, and a temporal duration of application of the energy.

4. The method according to claim 3, wherein computing the respective measures comprises computing an integral over the temporal duration of a product of the force raised to a first non-unity exponent and the power raised to a second non-unity exponent.

5. The method according to claim 1, wherein applying the energy comprises creating a line of the lesions in the tissue, and wherein generating the indication comprises evaluating an integrity of the line by computing the indication of contiguity between neighboring pairs of the lesions along the line.

6. The method according to claim 1, wherein generating the indication comprises computing the indication while applying the energy, and controlling application of the energy responsively to the indication.

7. The method according to claim 6, wherein applying the energy comprises, after having created the first lesion, continuing to apply the energy at the second site until the computed indication is within a predefined target range.

8. The method according to claim 1, wherein generating the indication comprises computing a weighted comparison between the first and second measures of the size of the lesions and the distance between the location coordinates of the first and second sites.

9. The method according to claim 8, wherein computing the weighted comparison comprises weighting each of the first and second measures responsively to a thickness of the tissue at each of the first and second sites.

10. The method according to claim 8, wherein computing the weighted comparison comprises weighting each of the first and second measures depending upon anatomical locations of the first and second sites.

11. The method according to claim 1, wherein applying the energy comprises ablating myocardial tissue in a heart of the patient.

12. Apparatus for performing a medical treatment, comprising:
an invasive probe, which is configured to apply energy to ablate tissue at a plurality of sites in an organ in a body of a patient, thereby creating lesions in the tissue including at least first and second lesions at respective first and second, mutually-adjacent sites; and
a processor, which is coupled to the probe and is configured to record location coordinates and respective treatment parameters at each of the sites with respect to the applied energy, and to compute, based on the recorded treatment parameters, respective measures of size of the lesions, including at least respective first and second measures of the first and second lesions, and to generate an indication of contiguity between at least the first and second lesions responsively to the first and second measures and to a distance between the location coordinates of the first and second sites, the generated indication of contiguity comprising at least one value computed by the processor, the at least one computed value based at least on the respective size measurements of the lesions and the distance between the location coordinates of the first and second sites.

13. The apparatus according to claim 12, wherein the applied energy comprises radio-frequency electrical energy applied through the probe while the probe contacts the tissue at each of the sites.

14. The apparatus according to claim 13, wherein the recorded treatment parameters comprise a force exerted by the probe against the tissue, a power of the electrical energy, and a temporal duration of application of the energy.

15. The apparatus according to claim 14, wherein the processor is configured to compute the respective measures of the size as an integral over the temporal duration of a product of the force raised to a first non-unity exponent and the power raised to a second non-unity exponent.

16. The apparatus according to claim 12, wherein the probe is configured to create a line of the lesions in the tissue, and wherein the processor is configured to evaluate an integrity of the line by computing the indication of contiguity between neighboring pairs of the lesions along the line.

17. The apparatus according to claim 12, wherein the processor is configured to compute the indication while the probe applies the energy, and to control application of the energy responsively to the indication.

18. The apparatus according to claim 17, wherein applying the energy comprises, after having created the first lesion, continuing to apply the energy at the second site until the computed indication is within a predefined target range.

19. The apparatus according to claim 12, wherein the indication comprises a weighted comparison between the first and second measures of the size of the lesions and the distance between the location coordinates of the first and second sites.

20. The apparatus according to claim 19, wherein the processor is configured to weight each of the first and second measures in the weighted comparison responsively to a thickness of the tissue at each of the first and second sites.

21. The apparatus according to claim 19, wherein the processor is configured to weight each of the first and second measures in the weighted comparison depending upon anatomical locations of the first and second sites.

22. The apparatus according to claim 12, wherein the probe comprises a catheter, which is configured to apply the energy so as to ablate myocardial tissue in a heart of the patient.

23. A computer software product, comprising a computer-readable medium in which program instructions are stored, which instructions are configured to be read and executed by a processor that is coupled to an invasive probe for ablating tissue at a plurality of sites in an organ in a body of a patient, thereby creating lesions in the tissue including at least first and second lesions at respective first and second, mutually-adjacent sites,
wherein the instructions cause the processor to record location coordinates and respective treatment parameters at each of the sites with respect to the applied energy, and to compute, based on the recorded treatment parameters, respective measures of size of the lesions, including at least respective first and second measures of the first and second lesions, and to generate an indication of contiguity between at least the first and second lesions responsively to the first and second measures and to a distance between the location coordinates of the first and second sites, the generated indication of contiguity comprising at least one value computed by the processor, the at least one computed value based at least on the respective size measurements of the lesions and the distance between the location coordinates of the first and second sites.

* * * * *